United States Patent [19]

Schnurr et al.

[11] Patent Number: 5,606,081
[45] Date of Patent: Feb. 25, 1997

[54] PREPARATION OF CYCLIC ETHER KETONES

[75] Inventors: Werner Schnurr, Herxheim; Rolf Fischer, Heidelberg, both of Germany

[73] Assignee: BASF Aktiengesellschaft, Ludwigshafen, Germany

[21] Appl. No.: 439,901

[22] Filed: May 12, 1995

[30] Foreign Application Priority Data

May 20, 1994 [DE] Germany .................. 44 17 696.1

[51] Int. Cl.$^6$ .................. C07D 309/12; C07D 307/20
[52] U.S. Cl. .................. 549/416; 549/346; 549/475; 549/510
[58] Field of Search .................. 549/416, 346, 549/475, 510

[56] References Cited

U.S. PATENT DOCUMENTS

| | | |
|---|---|---|
| 3,496,197 | 2/1970 | Van Rheemen . |
| 3,767,711 | 10/1973 | Gobron et al. . |
| 3,855,304 | 12/1974 | Sakakibara et al. . |
| 4,000,199 | 12/1976 | Obenaus et al. . |
| 4,120,824 | 10/1978 | Kruse ..................... 252/447 |
| 4,200,589 | 4/1980 | Scharf . |
| 4,250,119 | 2/1981 | Scharf et al. . |

FOREIGN PATENT DOCUMENTS

| | | |
|---|---|---|
| 1768116 | 10/1971 | Germany . |
| 2157307 | 5/1972 | Germany . |
| 2415151 | 10/1975 | Germany . |
| 2738269 | 3/1979 | Germany . |
| 1956018 | 5/1979 | Germany . |
| 2802672 | 7/1979 | Germany . |
| 2848400 | 5/1980 | Germany . |
| 1133882 | 11/1968 | United Kingdom . |
| 2038320 | 7/1980 | United Kingdom . |

OTHER PUBLICATIONS

Chem Ber. 109 (1976) 3707 to 3727.
J. Mol. Cat. 72(1992) 143 to 152.
J. Am. Chem. Soc. 1992, 114, 3685 – 6392.

*Primary Examiner*—Nicky Chan
*Attorney, Agent, or Firm*—Keil & Weinkauf

[57] ABSTRACT

A process for the preparation of a cyclic ether ketone of the general formula I $$O\underset{(CHR^1)_n}{\overset{(CHR^2)_m}{\diagup\!\!\!\diagdown}}C=O, \quad (I)$$

in which $R^1$ and $R^2$ denote hydrogen or $C_1$–$C_4$ alkyl, m and n denote integers from 1 to 5, in which a cyclic ether aldehyde of the general formula I $$O\underset{(CHR^1)_n}{\overset{(CHR^2)_m}{\diagup\!\!\!\diagdown}}CH-CHO, \quad (II)$$

in which have $R^1$, $R^2$, m and n have the above meanings, is reacted with an oxygen-containing gas in the presence of a solid or supported catalyst containing copper and/or manganese, at temperatures of from 50° to 300° C. and pressures of from 0.01 to 10 bar.

10 Claims, No Drawings

PREPARATION OF CYCLIC ETHER KETONES

The present invention relates to a process for the preparation of cyclic ether ketones from cyclic ether aldehydes using oxygen-containing gases in the presence of a solid or supported catalyst containing copper and/or manganese, at elevated temperatures.

Aldehydes such as isobutyraldehyde or aldehyde steriods can be converted to ketones by oxidative decarbonylization in the liquid phase. Catalysts used are, e.g., copper(II) acetate in the presence of a nitrogenous base (DE-A 1,768,116, GB-A 1,133,882) or molybdenum oxide (DE-A 1,956,018).

The conversion of isobutyraldehyde to acetone in the gas phase over supported copper or manganese catalysts at high yields is disclosed by DE-A 2,802,672, DE-A 2,738,269, DE-A 2,415,151, and DE-A 2,157,307. The method could be applied, using comparable catalyst systems, to other aliphatic aldehydes (DE-A 2,848,400).

It has also been disclosed that cyclic ethers are oxidized even under mild reaction conditions (25° C. or above) in the α-position to form lactones (*Chem. Ber.* 109 (1976) 3707 to 3727; *J. Mol. Cat.* 72 (1992) 143 to 152; *J. Am. Chem. Soc.* 114 (1992) 6385 to 6392).

It was thus the object of the present invention to overcome the aforementioned drawbacks.

Accordingly, we have found a novel process for the preparation of cyclic ether ketones of the general formula I

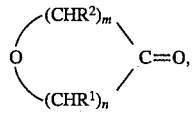  (I)

in which $R^1$ and $R^2$ denote hydrogen or $C_1$–$C_4$ alkyl, m and n denote integers from 1 to 5, wherein cyclic ether aldehydes of the general formula II

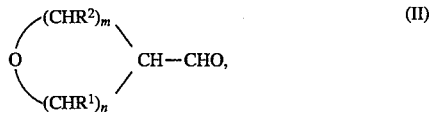  (II)

in which have $R^1$, $R^2$, m and n have the above meanings, are reacted with oxygen-containing gases in the presence of a solid or supported catalyst containing copper and/or manganese, at temperatures of from 50° to 300° C. and pressures of from 0.01 to 10 bar.

Suitable starting materials are formyl-substituted cyclic ethers having a ring size of from 4 to 12 (m and n=1 to 5) and preferably from 5 to 7. 4-Formyltetrahydropyran is particularly preferred.

The substituents $R^1$ and $R^2$ and the indices m and n have the following meanings:

$R^1$ and $R^2$ hydrogen or $C_1$–$C_4$ alkyl such as methyl, ethyl, n-propyl, isopropyl, n-butyl, isobutyl, sec-butyl and tert- butyl, preferably methyl and ethyl and more preferably methyl, m and n an integer from 1 to 5, preferably from 1 to 4 and more preferably from 1 to 3.

Suitable catalysts are those containing copper and/or manganese. They may be solid or supported catalysts. The total content of copper and/or manganese should usually be from 0.1 to 50 wt %, preferably from 1 to 20 wt % and more preferably from 1.5 to 10 wt %. A positive effect on the selectivity is achieved by adding zinc oxide usually in amounts ranging from 0.4 to 40 wt %, preferably from 1 to 20 wt % and more preferably from 2 to 10 wt %.

Suitable support materials have been found to be aluminum oxide, silicon dioxide, titanium dioxide, zirconium dioxide, aluminum silicates, magnesium silicates, or mixtures thereof. It is preferred to use aluminum oxide, titanium dioxide, and magnesium silicate. Such catalysts can be prepared in known manner by impregnation of preformed supports such as pellets, balls, or extrudates, e.g., using an aqueous solution of the metal salts which convert to their oxides on heating.

The supported catalysts preferably used show high activity over a prolonged period. Spent catalysts can be regenerated by treatment with oxygen-containing gases, e.g. air, at temperatures of from 350° to 500° C.

During the oxidative decarbonylization a temperature of from 50° to 300° C., preferably from 100° to 250° C., in particular of from 120° to 200° C. is maintained. The oxidation can preferably be carried out at pressures ranging from 0.01 to 10 bar and more preferably from 0.1 to 2 bar, particularly standard pressure (atmospheric pressure).

The process is usually carried out at a specific throughput of from 0.01 to 10, preferably from 0.01 to 3 kg of aldehyde per kilogram of catalyst per hour.

Suitable oxidizing agents are oxygen-containing gases, preferably air. The oxygen concentration in the starting gas depends on the aldehyde concentration. The molar ratio of oxygen in the oxygen-containing gas to the aldehyde is usually from 1:1 to 200:1, preferably from 1.1:1 to 10:1 and more preferably from 1.5:1 to 5:1.

The addition of an inert diluent is also advantageous. It is usual to use nitrogen, water, carbon monoxide, or carbon dioxide. It is preferred to add nitrogen and/or steam.

The reaction can be carried out in the liquid phase but preferably in the gas phase, batchwise or preferably continuously as a fixed bed reaction using a fixed catalyst, employing, for example, an upflow or trickle procedure, or as a fluid bed reaction using a catalyst which is intermittently fluidized.

The process of the invention makes it possible to selectively prepare hitherto difficultly available ketones in a simple manner.

EXAMPLES

Example 1

(Preparation of Catalyst)

A solution of 25.1 g of zinc(II) nitrate in 70 mL of water is added to 150 g of aluminum oxide (1.5 mm extrudates). Following drying at 110° C. (15 h) the extrudates are tempered for 15 h at 350° C. in air. A solution of 24.5 g of copper(II) nitrate in 70 mL of water is then added to the pretreated aluminum oxide, and the mixture is dried and calcined (see above). The finished catalyst contains 4.1 wt % of copper and 3.7 wt % of zinc.

Example 2

(Preparation of Catalyst)

A solution of 15.2 g of copper(II) nitrate in 47 mL of water is added to 100 g of aluminum oxide (1.5 mm extrudates). Following drying at 110° C. (15 h) the extrudates are tempered for 15 h at 350° C. in air. The finished catalyst contains 3.8 wt % of copper.

Example 3

(Preparation of Catalyst)

A solution of 18.3 g of manganese(II) nitrate in 47 mL of water is added to 100 g of aluminum oxide (1.5 mm extrudates). Following drying at 110° C. (15 h) the extrudates are tempered for 15 h at 350° C. in air. The finished catalyst contains 3.7 wt % of manganese.

Example 4

(Preparation of Catalyst)

A solution of 18.3 g of manganese(II) nitrate in 47 mL of water is added to 100 g of aluminum oxide (1.5 mm extrudates). Following drying at 110° C. (15 h) the extrudates are tempered for 15 h at 350° C. in air. A solution of 16 g of zinc(II) nitrate in 47 mL of water is then added to the pretreated aluminum oxide, and the mixture is dried and calcined (see above). The finished catalyst contains 3.5 wt % of manganese and 3.7 wt % of zinc.

Example 5

11 g per hour of a solution, which consists of 20 wt % 4-formyltetrahydropyran and 80 wt % of water, are pumped into an evaporator (at from 200° to 250° C.) and passed from said evaporator, together with a mixture of 17.5 L/h of nitrogen and 2.5 L/h of oxygen at a reactor temperature of 150° C., over 66 g of catalyst (Example 1) by a trickling procedure. The gaseous effluent is condensed in cold traps and analyzed by gas chromatography (quantitative gas chromatography). There are formed 85 mol % of tetrahydropyran-4-one. The aldehyde conversion is greater than 99%.

Example 5

3 g per hour of 4-formyltetrahydropyran are pumped into an evaporator (at from 200° to 250° C.) and passed from said evaporator, together with a mixture of 32.5 L/h of nitrogen and 2.5 L/h of oxygen at a reactor temperature of 1 50° C., over 66 g of catalyst (Example 1) by a trickling procedure. The gaseous effluent is condensed in cold traps and analyzed by gas chromatography (quantitative gas chromatography). There are formed 81 mol % of tetrahydropyran-4-one. The aldehyde conversion is more than 87%.

Example 7

13 g per hour of a solution, which consists of 20 wt % of 4-formyltetrahydropyran and 80 wt % of water, are pumped into an evaporator (at from 200° to 250° C.) and passed from said evaporator, together with a mixture of 17.5 L/h of nitrogen and 2.5 L/h of oxygen at a reactor temperature of 150° C., over 68 g of catalyst (Example 2) by a trickling procedure. The gaseous effluent is condensed in cold traps and analyzed by gas chromatography (quantitative gas chromatography). There are formed 75 mol % of tetrahydropyran-4-one. The aldehyde conversion is 99%.

Example 8

11 g per hour of a solution, which consists of 20 wt % 4-formyltetrahydropyran and 80 wt % of water, are pumped into an evaporator (at from 200° to 250° C.) and passed from said evaporator, together with a mixture of 17.5 L/h of nitrogen and 2.5 L/h of oxygen at a reactor temperature of 150° C., over 64 g of catalyst (Example 3) by a trickling procedure. The gaseous effluent is condensed in cold traps and analyzed by gas chromatography (quantitative gas chromatography). There are formed 44 mol % of tetrahydropyran-4-one. The aldehyde conversion is 99%.

Example 9

11 g per hour of a solution, which consists of 20 wt % 4-formyltetrahydropyran and 80 wt % of water, are pumped into an evaporator (at from 200° to 250° C.) and passed from said evaporator, together with a mixture of 17.5 L/h of nitrogen and 2.5 L/h of oxygen at a reactor temperature of 150° C., over 69 g of catalyst (Example 4) by a trickling procedure. The gaseous effluent is condensed in cold traps and analyzed by gas chromatography (quantitative gas chromatography). There are formed 48 mol % of tetrahydropyran-4-one. The aldehyde conversion is 97%.

We claim:

1. A process for the preparation of a cyclic ether ketone of the general formula I

in which $R^1$ and $R^2$ denote hydrogen or $C_1$–$C_4$ alkyl, m and n denote integers from 1 to 5, wherein a cyclic ether aldehyde of the general formula II

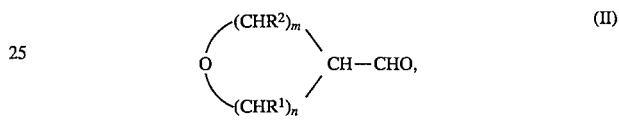

in which have $R^1$, $R^2$, m and n have the above meanings, is reacted with an oxygen-containing gas in the presence of a solid or supported catalyst containing copper and/or manganese, at temperatures of from 50° to 300° C. and pressures of from 0.01 to 10 bar.

2. A process for the preparation of a cyclic ether ketone I as defined in claim 1, wherein a supported catalyst is used in which the total content of copper and/or manganese is from 0.1 to 50 wt %.

3. A process for the preparation of a cyclic ether ketone I as defined in claim 1, wherein a supported catalyst is used in which the total content of copper and/or manganese is from 0.1 to 50 wt % and which contains from 0.4 to 40 wt % of zinc oxide.

4. A process for the preparation of a cyclic ether ketone I as defined in claim 1, wherein a supported catalyst is used which has a support material selected from the group comprising aluminum oxide, silicon dioxide, titanium dioxide, zirconium dioxide, aluminum silicates, magnesium silicates, or mixtures thereof.

5. A process for the preparation of a cyclic ether ketone I as defined in claim 1, which is carried out at temperatures of from 100° to 250° C.

6. A process for the preparation of a cyclic ether ketone I as defined in claim 1, wherein the molar ratio of oxygen in the oxygen-containing gas to the aldehyde is from 1:1 to 200:1.

7. A process for the preparation of a cyclic ether ketone I as defined in claim 1, wherein air is used as the oxygen-containing gas.

8. A process for the preparation of a cyclic ether ketone I as defined in claim 1 wherein the reaction is carried out in the presence of an inert diluent.

9. A process for the preparation of a cyclic ether ketone I as defined in claim 8, wherein the inert diluent used is nitrogen, steam or a mixture thereof.

10. A process for the preparation of a cyclic ether ketone II as defined in claim 1, wherein, in the formulas I and II: $R^1$ and $R^2$ denote hydrogen, and m and n are both equal to 2.

* * * * *

UNITED STATES PATENT AND TRADEMARK OFFICE
CERTIFICATE OF CORRECTION

PATENT NO.: 5,606,081

DATED: February 25, 1997

INVENTOR(S): SCHNURR et al.

It is certified that error appears in the above-identified patent and that said Letters Patent is hereby corrected as shown below:

On the cover page, in the Abstract, item [57], line 6, "general formula I" should read --general formula II--.

Signed and Sealed this

Fifteenth Day of April, 1997

Attest:

BRUCE LEHMAN

*Attesting Officer*  Commissioner of Patents and Trademarks